United States Patent
Mezei et al.

(10) Patent No.: US 7,060,842 B2
(45) Date of Patent: Jun. 13, 2006

(54) METHOD FOR SYNTHESIS OF (2S, 3AS, 7AS)-1-{(S)-ALANYL}-OCTAHYDRO-1H-INDOLE-2-CARBOXYLIC ACID DERIVATIVES AND USE FOR SYNTHESIS OF PERINDOPRIL

(75) Inventors: Tibor Mezei, Budapest (HU); Marta Porcs-Makkay, Pomaz (HU); Gyula Simig, Budapest (HU)

(73) Assignee: Les Laboratoires Servier, Courbevoie (FR)

( * ) Notice: Subject to any disclaimer, the term of this patent is extended or adjusted under 35 U.S.C. 154(b) by 313 days.

(21) Appl. No.: 10/484,022

(22) PCT Filed: Jul. 23, 2002

(86) PCT No.: PCT/FR02/02627

§ 371 (c)(1),
(2), (4) Date: Jan. 15, 2004

(87) PCT Pub. No.: WO03/016336

PCT Pub. Date: Feb. 27, 2003

(65) Prior Publication Data

US 2004/0198988 A1 Oct. 7, 2004

(30) Foreign Application Priority Data

Jul. 24, 2001 (FR) .................... 01 09839

(51) Int. Cl.
*C07D 209/04* (2006.01)
(52) U.S. Cl. ..................................... 548/452
(58) Field of Classification Search ............... 548/452
See application file for complete search history.

(56) References Cited

FOREIGN PATENT DOCUMENTS

| EP | 0049658 A | 4/1982 |
|----|-----------|--------|
| EP | 0308341 A | 3/1989 |
| WO | WO/01/56353 A | 8/2001 |
| WO | WO/01/56972 A | 8/2001 |
| WO | WO/01/58868 A | 8/2001 |

OTHER PUBLICATIONS

L. Pichat, et al. Journal of Labelled Compounds and Radiopharmaceuticals, 25(5): 553-568, 1987.*
Vincent, M., et al.: Drug Design and Discovery, Harwood Academic Pub-lishers GMBH, XX, vol. 9, No. 1, 1992, pp. 11-28. Title: Synthesis and ACE Inhibitory Activity of the Stereoisomers of Perindopril (S 9490) and Peripdoprilate (S 9780).

* cited by examiner

*Primary Examiner*—Kamal A. Saeed
*Assistant Examiner*—Michael P. Barker
(74) *Attorney, Agent, or Firm*—Hueschen and Sage

(57) ABSTRACT

Process for the industrial synthesis of the compounds of formula (I):

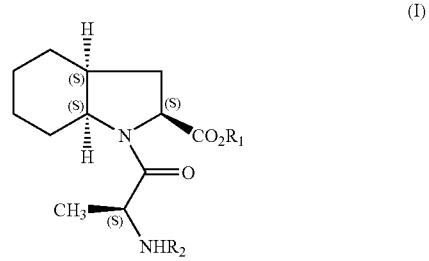

(I)

wherein $R_1$ represents a hydrogen atom or an alkyl or benzyl group, and $R_2$ represents a group that protects the amino function.

8 Claims, No Drawings

METHOD FOR SYNTHESIS OF (2S, 3AS, 7AS)-1-{(S)-ALANYL}-OCTAHYDRO-1H-INDOLE-2-CARBOXYLIC ACID DERIVATIVES AND USE FOR SYNTHESIS OF PERINDOPRIL

The present invention relates to a process for the industrial synthesis of compounds of formula (I):

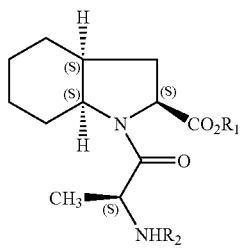

wherein $R_1$ represents a hydrogen atom, a linear or branched ($C_1$–$C_6$)alkyl group or a benzyl group, and $R_2$ represents a group that protects the amino function, and to their application in the industrial synthesis of perindopril of formula (II):

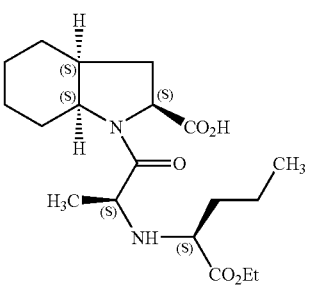

and of its pharmaceutically acceptable salts.

Perindopril, and also pharmaceutically acceptable salts thereof, and more especially the tert-butylamine salt thereof, have valuable pharmacological properties. Their principal property lies in the inhibition of the enzyme that converts angiotensin I (or kininase II), which enables on the one hand prevention of the conversion of the decapeptide angiotensin I to the octapeptide angiotensin II (vasoconstrictor), and on the other hand prevention of the degradation of bradykinin (vasodilator) to inactive peptide. Those two actions contribute to the beneficial effects of perindopril in cardiovascular disorders, especially arterial hypertension and cardiac insufficiency.

Perindopril, its preparation and its therapeutic use have been described in European Patent EP0049658.

Given the pharmaceutical value of that compound, it is important to be able to obtain it by an effective industrial synthesising process that can readily be applied on an industrial scale, yielding perindopril in a good yield and, especially, with an excellent degree of purity.

Patent Specification EP 0 308 341 describes the industrial synthesis of perindopril by catalytic hydrogenation of (2S)-2,3-dihydroindole-2-carboxylic acid, followed by coupling of the resulting (2S, 3aS, 7aS)-octahydroindole-2-carboxylic acid benzyl ester with N-[(S) -1-carboxybutyl]-(S)-alanine ethyl ester, and then deprotection of the carboxylic group of the heterocycle by catalytic hydrogenation.

That process has the advantage of yielding perindopril in a good yield. However, the purity of the perindopril obtained by that process is not satisfactory, and necessitates a purification step in order to obtain perindopril of a quality that would allow its use as a pharmaceutical active ingredient. Indeed, under the conditions described in that patent specification the perindopril obtained is contaminated by significant amounts of the impurities of formulae (III) and (IV):

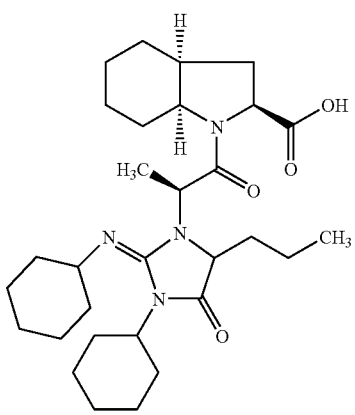

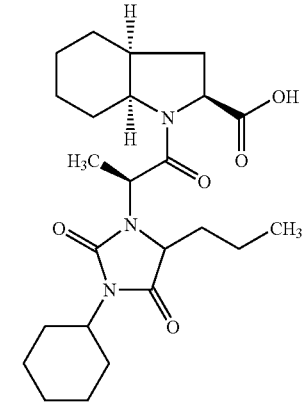

The Applicant has now developed a new industrial synthesising process that, without requiring laborious purification, yields perindopril of a purity that is compatible with its use as a pharmaceutical active ingredient, and that is, for example, totally free of the impurities of formulae (III) and (IV).

Moreover, the process uses alanine as its source of chirality, alanine being a natural and, accordingly, inexpensive starting material.

More specifically, the present invention relates to a process for the industrial synthesis of the compound of formula (I):

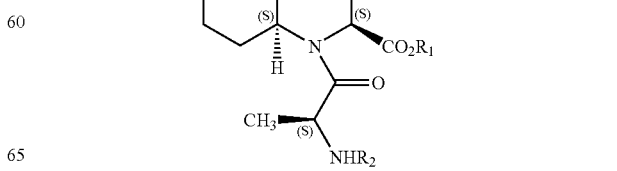

wherein $R_1$ represents a hydrogen atom, a linear or branched $(C_1-C_6)$alkyl group or a benzyl group, and $R_2$ represents a group that protects the amino function, characterised in that the ester of formula (V):

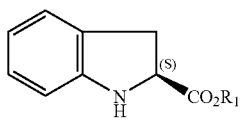

(V)

wherein $R_1$ is as defined for formula (I), is reacted with the alanine compound of formula (VI):

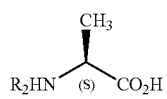

(VI)

wherein $R_2$ is as defined for formula (I), in an organic solvent, such as, for example, tetrahydrofuran or ethyl acetate, in the absence of 1-hydroxybenzotriazole or in the presence of an amount of less than 0.6 mol of 1-hydroxybenzotriazole per mol of compound of formula (V) employed, in the presence of an amount of from 1 to 1.2 mol of dicyclohexylcarbodiimide per mol of compound of formula (V) employed, and in the presence of an amount of from 1 to 1.2 mol of triethylamine per mol of compound of formula (V) employed, at a temperature of from 20 to 50° C., to yield, after isolation and then recrystallisation, the compound of formula (VII):

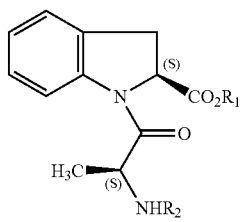

(VII)

wherein $R_1$ and $R_2$ are as defined hereinbefore, which is hydrogenated in the presence of a catalyst, such as, for example, Pd/C, Rh/C, Pt/C, Ni/C or $PtO_2$, under a hydrogen pressure of from 1 to 40 bars, at a temperature of from 30 to 70° C., to yield the compound of formula (I).

The compound of formula (I) so obtained is then subjected, where appropriate, to a reaction for the deprotection of the acid and amine functions, followed by a coupling reaction, either with ethyl 2-oxo-pentanoate under conditions of reductive amination, or with a compound of formula (XII):

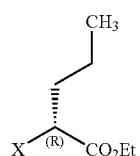

(XII)

wherein X represents a leaving group selected from a halogen atom, $-O-SO_2CH_3$ and

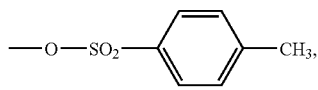

to yield optically pure perindopril, which is converted, if desired, into a pharmaceutically acceptable salt such as the tert-butylamine salt.

The process is of particular interest for the following reasons:

The coupling in alkaline medium of the (2S, 3aS, 7aS)-octahydroindole-2-carboxylic acid benzyl ester of formula (VIII):

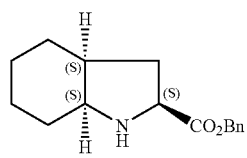

(VIII)

with the compound of formula (IX) has been described in Patent Specification EP 0 308 341.

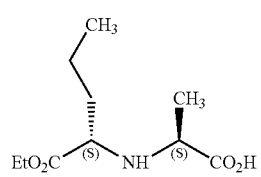

(IX)

However, the perindopril benzyl ester so obtained is contaminated by a number of by-products.

In particular, it contains significant amounts (5 to 15%) of the impurities of formulae (X) and (XI) resulting from the reaction of the coupling product with dicyclohexylcarbodiimide, which impurities, after debenzylation, yield the impurities of formulae (III) and (IV).

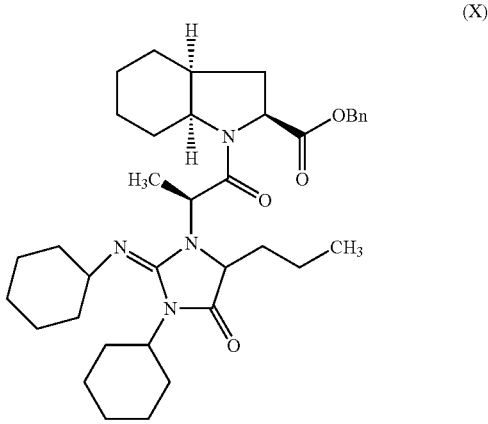

(X)

-continued

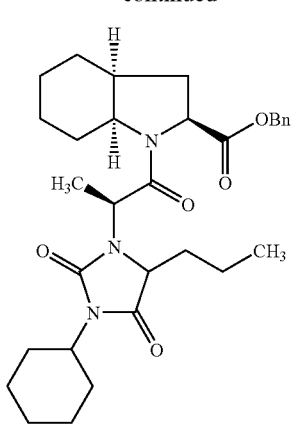
(XI)

The Applicant has found that the coupling reaction of the compound of formula (V) with the compound of formula (VI) yields a compound of formula (VII) that is totally free of the impurities resulting from the reaction of the coupling product with dicyclohexylcarbodiimide.

The compound of formula (VII) so obtained yields perindopril of far better purity, and that is in particular totally free of the impurities of formulae (III) and (IV).

Moreover, the Applicant has found that it was possible to obtain the intermediate compound of formula (VII) in a crystalline form that was readily purifiable. Its conversion according to the process of the invention thus yields the compound of formula (I) in excellent purity.

The Examples below illustrate the invention, but do not limit it in any way.

EXAMPLE 1

Methyl(2S)-1-{(2S)-2-[(tert-butyloxycarbonyl)-amino]-propionyl}-2,3-dihydro-1H-indole-2-carboxylate There are introduced into a reactor, with stirring, 2.13 kg of methyl(2S)-2,3-dihydroindole-2-carboxylate, 1 kg of triethylamine, 30 litres of tetrahydrofuran and then, after 10 minutes' stirring at room temperature, 1.9 kg of N-[tert-butyloxycarbonyl]-(S)-alanine and 2 kg of dicyclohexylcarbodiimide. The heterogeneous mixture is then stirred at room temperature for 6 hours, and is subsequently cooled to 0° C. and filtered.

The filtrate is then washed and recrystallised from a mixture of hexane/ethyl acetate 10/1 to yield the expected product in a yield of 81% and with a chemical purity of 98%.

Melting Point: 130–131° C.

Elemental Microanalysis:

|  | C% | H% | N% |
| --- | --- | --- | --- |
| calculated | 62.05 | 6.94 | 8.04 |
| found | 61.80 | 6.94 | 8.00 |

EXAMPLE 2

Methyl(2S, 3aS, 7aS)-1-{(2S)-2-[(tert-butyloxycarbonyl)-amino]-propionyl}-octahydro-1H-indole-2-carboxylate/method 1

The residue obtained in Example 1 (1 kg) is dissolved in methanol and transferred to a hydrogenator, and then 0.10 kg of 5% rhodium-on-carbon is added.

The mixture is then hydrogenated under a pressure of 30 bars, at a temperature of 60° C., until absorption of the theoretical amount of hydrogen.

After removal of the catalyst by filtration, the solvent is removed by evaporation to yield the expected product in a yield of 90% and with a chemical purity of 98%.

EXAMPLE 3

Methyl(2S, 3aS, 7aS)-1-{(2S)-2-[(tert-butyloxycarbonyl)-amino]-propionyl}-octahydro-1H-indole-2-carboxylate/method 2

The residue obtained in Example 1 (1 kg) is dissolved in acetic acid and transferred to a hydrogenator, and then 0.10 kg of platinum dioxide is added.

The mixture is then hydrogenated under a pressure of 10 bars at a temperature of 40° C., until absorption of the theoretical amount of hydrogen.

After removal of the catalyst by filtration, the solvent is removed by evaporation to yield the expected product in a yield of 90% and with a chemical purity of 98%.

The invention claimed is:

1. A process for the industrial synthesis of a compound selected from those of formula (I):

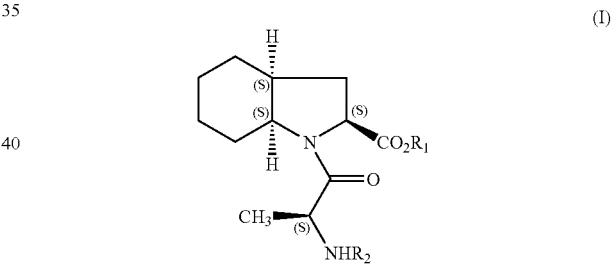
(I)

wherein $R_1$ represents hydrogen, linear or branched ($C_1$–$C_6$) alkyl or benzyl, and $R_2$ represents a group that protects the amino function, wherein the ester of formula (V):

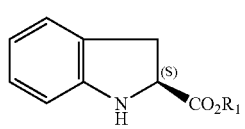
(V)

is reacted with the alanine compound of formula (VI):

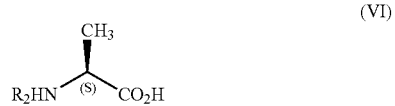
(VI)

in an organic solvent in the absence of 1-hydroxybenzotriazole or in the presence of an amount of less than 0.6 mol of 1-hydroxybenzotriazole per mol of compound of formula (V) employed, in the presence of an amount of 1 to 1.2 mol of dicyclohexylcarbodiimide per mol of compound of formula (V) employed, and in the presence of an amount of 1 to 1.2 mol of triethylamine per mol of compound of formula (V) employed, at a temperature of 20 to 50° C., to yield, after isolation and then recrystallisation, the compound of formula (VII):

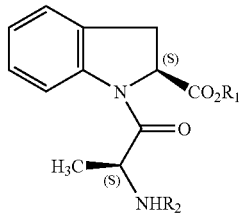

(VII)

which is hydrogenated in the presence of a catalyst under a hydrogen pressure of 1 to 40 bars, at a temperature of 30 to 70° C., to yield the compound of formula (I).

2. A process according to claim 1, wherein the organic solvent is selected from tetrahydrofuran or ethyl acetate.

3. A process according to claim 1, wherein the catalyst is selected from Pd/C, Rh/C, Pt/C, Ni/C or PtO$_2$.

4. A process according to claim 3, wherein the catalyst employed in the hydrogenation step is rhodium-on-carbon.

5. A process according to claim 3, wherein the catalyst employed in the hydrogenation step is platinum dioxide.

6. A process according to claim 1, wherein R$_1$ represents methyl.

7. Process for the synthesis of perindopril or pharmaceutically acceptable salts thereof, using a compound of formula (I) obtained by the process of claim 1, wherein the compound of formula (I) is subjected, where appropriate, to a reaction for the deprotection of acid and amine functions, followed by a coupling reaction with ethyl 2-oxo-pentanoate under reductive amination conditions, or with a compound of formula (XII):

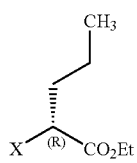

(XII)

wherein X represents a leaving group selected from a halogen atom, —O—SO$_2$CH$_3$ and

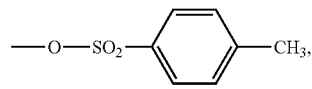

to yield optically pure perindopril, which is converted, if desired, into a pharmaceutically acceptable salt.

8. Process of claim 7 wherein the resulting perindopril is free of the impurities of formulae (III) and (IV).

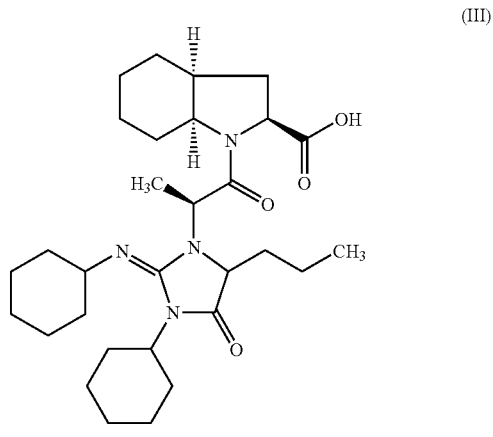

(III)

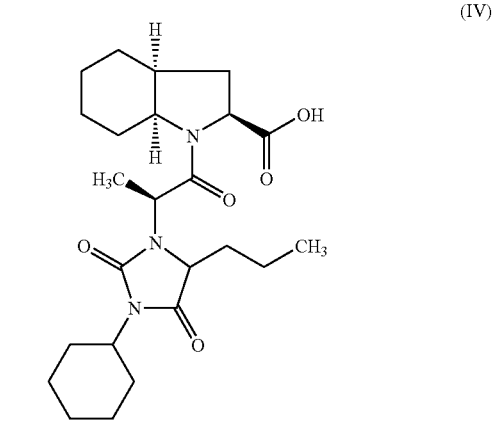

(IV)

* * * * *

UNITED STATES PATENT AND TRADEMARK OFFICE
CERTIFICATE OF CORRECTION

PATENT NO. : 7,060,842 B2
APPLICATION NO. : 10/484022
DATED : June 13, 2006
INVENTOR(S) : Tibor Mezei et al.

Page 1 of 1

It is certified that error appears in the above-identified patent and that said Letters Patent is hereby corrected as shown below:

Title Page, Item (57) Abstract: The last sentence of the abstract is missing. Please add the Following: --Application in the synthesis of perindopril and of its pharmaceutically acceptable salts.--

Signed and Sealed this

Twenty-sixth Day of September, 2006

JON W. DUDAS
*Director of the United States Patent and Trademark Office*